(12) United States Patent
Okaniwa et al.

(10) Patent No.: US 10,799,091 B2
(45) Date of Patent: Oct. 13, 2020

(54) ENDOSCOPE WITH MESH TUBE

(71) Applicant: OLYMPUS CORPORATION, Tokyo (JP)

(72) Inventors: Suguru Okaniwa, Hachioji (JP); Seisuke Takase, Hachioji (JP); Hidehiro Joko, Hachioji (JP); Isamu Nakajima, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 395 days.

(21) Appl. No.: 15/978,256

(22) Filed: May 14, 2018

(65) Prior Publication Data

US 2018/0256010 A1 Sep. 13, 2018

Related U.S. Application Data

(63) Continuation of application No. PCT/JP2016/084050, filed on Nov. 17, 2016.

(30) Foreign Application Priority Data

Nov. 20, 2015 (JP) .................................. 2015-227904

(51) Int. Cl.
*A61B 1/00* (2006.01)
*G02B 23/24* (2006.01)
*A61B 1/005* (2006.01)

(52) U.S. Cl.
CPC ............ *A61B 1/00078* (2013.01); *A61B 1/00* (2013.01); *A61B 1/0055* (2013.01);
(Continued)

(58) Field of Classification Search
CPC ............ A61B 1/00078; A61B 1/00071; A61B 1/0055; A61B 1/0057; A61B 1/00133;
(Continued)

(56) References Cited

U.S. PATENT DOCUMENTS 5,788,714 A * 8/1998 Ouchi ................ A61B 1/00071
138/123
6,013,047 A * 1/2000 King ................. A61M 25/0045
604/22

(Continued)

FOREIGN PATENT DOCUMENTS

EP 2853189 A1 4/2015
JP H10-276965 A 10/1998
(Continued)

OTHER PUBLICATIONS

International Search Report dated Feb. 21, 2017 issued in PCT/JP2016/084050.

*Primary Examiner* — John P Leubecker
(74) *Attorney, Agent, or Firm* — Scully, Scott, Murphy & Presser, P.C.

(57) ABSTRACT

An endoscope includes: an insertion portion formed in an elongated shape; a mesh tube formed by braiding thin wires in a tubular shape and provided in a shape of a cylinder inside the insertion portion; and a rigidity changing mechanism including a coil inserted in the insertion portion and formed by winding an element wire, and a wire inserted in the coil and formed by intertwining element wires, the rigidity changing mechanism being configured to apply a compression force to the coil by pulling the wire, to adjust a bending rigidity of the insertion portion, wherein a dimension of a gap created between the thin wires in the mesh tube is set to be smaller than a diameter of the wire and larger than a diameter of each of the element wires of the wire.

5 Claims, 2 Drawing Sheets

(52) U.S. Cl.
CPC ............ *A61B 1/0057* (2013.01); *G02B 23/24* (2013.01); *A61B 1/00096* (2013.01); *A61B 1/00133* (2013.01); *G02B 23/2476* (2013.01)

(58) Field of Classification Search
CPC ... A61B 1/0011; G02B 23/24; G02B 23/2476
See application file for complete search history.

(56) References Cited

U.S. PATENT DOCUMENTS

| | | | |
|---|---|---|---|
| 2002/0002323 A1* | 1/2002 | Moriyama | A61B 1/00071 600/140 |
| 2002/0019582 A1* | 2/2002 | Takase | A61B 1/00071 600/140 |
| 2007/0161291 A1* | 7/2007 | Swinehart | A61B 1/0055 439/607.41 |
| 2013/0041224 A1* | 2/2013 | Okaniwa | A61B 1/0056 600/142 |
| 2015/0087905 A1 | 3/2015 | Ueda | |

FOREIGN PATENT DOCUMENTS

| | | |
|---|---|---|
| JP | H11-178784 A | 7/1999 |
| JP | 2006-055664 A | 3/2006 |
| JP | 2007-325748 A | 12/2007 |
| JP | 2015-065976 A | 4/2015 |

\* cited by examiner

ENDOSCOPE WITH MESH TUBE

CROSS REFERENCE TO RELATED APPLICATIONS

This application is a continuation application of PCT/JP2016/084050 filed on Nov. 17, 2016 and claims benefit of Japanese Application No. 2015-227904 filed in Japan on Nov. 20, 2015, the entire contents of which are incorporated herein by this reference.

BACKGROUND OF THE INVENTION

1. Field of the Invention

The present invention relates to an endoscope including linear members inserted in an insertion portion of the endoscope.

2. Description of the Related Art

For the purpose of observing a site where observation is difficult, such as an inside of a living body or structure, an endoscope including an image pickup unit for picking up an optical image in a distal end portion of an insertion portion insertable from an outside into an inside of a living body or structure has been used in medical fields or industrial fields, for example.

The endoscope disclosed in Japanese Patent Application Laid-Open Publication No. 10-276965 includes a rigidity changing mechanism portion that changes rigidity in a bending direction of a part of the insertion portion. The rigidity changing mechanism portion includes a coil pipe inserted in the insertion portion, a wire inserted in the coil pipe, and a pulling mechanism portion that applies a compression force to the coil pipe by pulling the wire. The rigidity of the coil pipe in the bending direction changes according to the applied compression force. Therefore, the rigidity of the part of the insertion portion in which the coil pipe is inserted changes according to the compression force applied to the coil pipe.

SUMMARY OF THE INVENTION

An endoscope according to one aspect of the present invention includes: an insertion portion formed in an elongated shape; a mesh tube formed by braiding thin wires in a tubular shape and provided in a shape of a cylinder inside the insertion portion; and a rigidity changing mechanism including a coil inserted in the insertion portion and formed by winding an element wire, and a wire inserted in the coil and formed by intertwining element wires, the rigidity changing mechanism being configured to apply a compression force to the coil by pulling the wire, to adjust a bending rigidity of the insertion portion, wherein a dimension of a gap created between the thin wires in the mesh tube is set to be smaller than a diameter of the wire and larger than a diameter of each of the element wires of the wire.

DETAILED DESCRIPTION OF THE PREFERRED EMBODIMENT(S)

Figure 1:
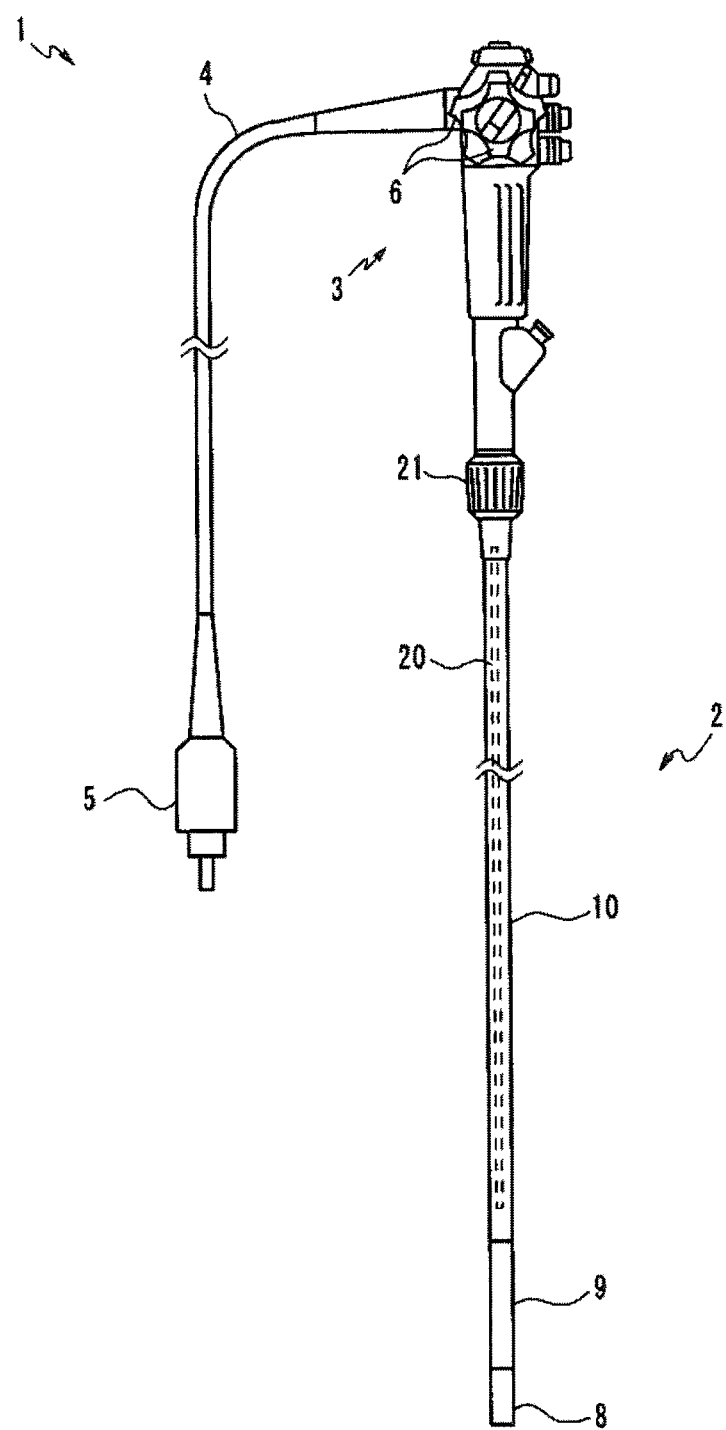
FIG. 1 illustrates a configuration of an endoscope.

Hereinafter, preferred embodiments of the present invention will be described with reference to drawings. Note that, in the drawings used for the description below, a different scale size is used for each of the components in order to allow each of the components to be illustrated in a recognizable size in the drawings, and the present invention is not limited to the number, shapes, ratio of the sizes of the components, and a relative positional relationship among the components shown in these drawings.

An endoscope 1 according to the present embodiment as shown in FIG. 1 includes an elongated insertion portion 2 configured to be introduceable into a subject such as a human body, and the endoscope includes, in the insertion portion 2, a configuration for observing the inside of the subject. Note that the subject into which the insertion portion 2 of the endoscope 1 is introduced is not limited to a human body, but may be another living body, or an artifact such as a machine, construction, and the like.

The endoscope 1 according to the present embodiment is mainly configured by the insertion portion 2 formed in an elongated shape so as to be introduced into a subject, an operation portion 3 located at the proximal end of the insertion portion 2, and a universal cord 4 extended from the operation portion 3.

The insertion portion 2 is configured by continuously including a distal end portion 8 disposed at the distal end of the insertion portion, a bendable bending portion 9 disposed at the proximal end side of the distal end portion 8, and a flexible tube portion 10 having flexibility and configured to connect the proximal end side of the bending portion 9 and the distal end side of the operation portion 3.

The distal end portion 8 includes, for example, a configuration for observing an inside of a subject. For example, the distal end portion 8 includes an image pickup unit including an objective lens and an image pickup device and configured to optically observe the inside of the subject. In addition, the distal end portion 8 also includes an illumination light emitting portion that emits light for illuminating an object of the image pickup unit, though not shown. Note that the distal end portion 8 may include an ultrasound transducer for sonically observing the inside of the subject by using ultrasound.

The operation portion 3, which is disposed at the proximal end of the insertion portion 2, is provided with an angle operating knob 6 for operating bending of the bending portion 9. At the proximal end portion of the universal cord 4, an endoscope connector 5 configured to be connectable to an external apparatus, not shown, is provided. The external apparatus to which the endoscope connector 5 is connected includes, for example, a camera control unit that controls the image pickup unit provided at the distal end portion 8.

In addition, the operation portion 3 is provided with a rigidity changing knob 21 for operating a rigidity changing mechanism portion 20 disposed in the flexible tube portion 10. The rigidity changing mechanism portion 20 is inserted in the flexible tube portion 10 along the longitudinal direction of the flexible tube portion 10, and configured such that the rigidity against curve changes according to the operation input by means of the rigidity changing knob 21. That is, the rigidity changing mechanism portion 20 changes the rigidity against curve of the flexible tube portion 10.

Figure 2:
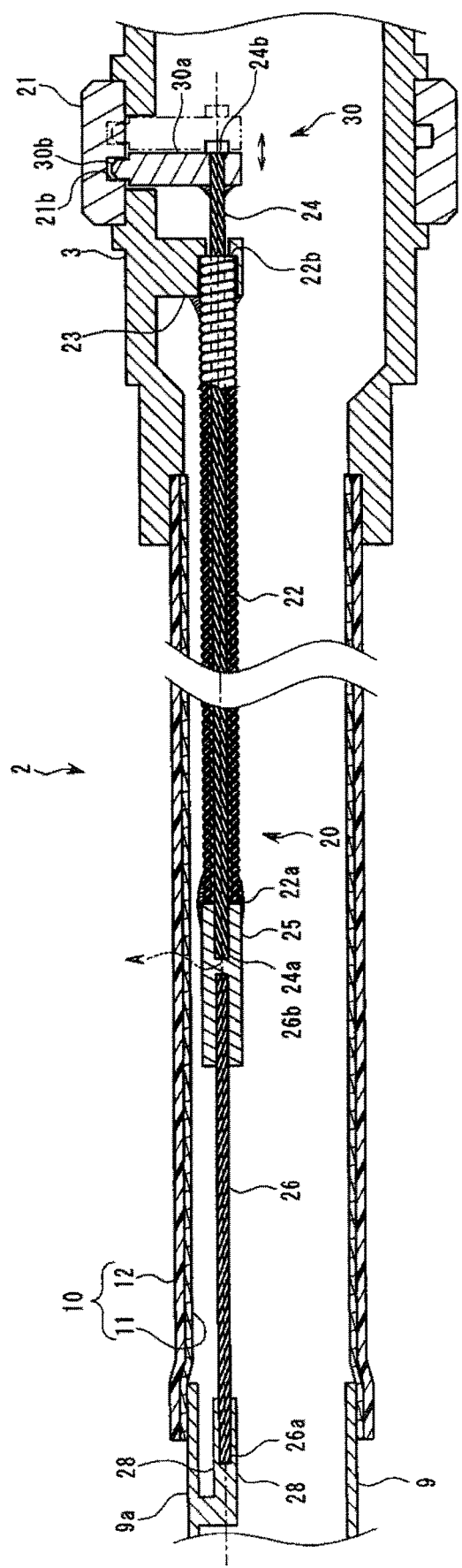
FIG. 2 illustrates configurations of a flexible tube portion and a rigidity changing mechanism portion.

Next, description will be made on the configurations of the flexible tube portion 10 and the rigidity changing mechanism portion 20. As shown in FIG. 2, the flexible tube portion 10 includes a mesh tube 11 and an outer cover 12.

The mesh tube 11 is formed by braiding thin wires made of metal such as stainless alloy in a tubular shape. The outer cover 12 is a film made of synthetic resin which covers the outer circumference of the mesh tube 11. The mesh tube 11 is covered with the outer cover 12, to thereby maintain the airtightness in the flexible tube portion 10. In other words, the mesh tube 11 is inserted in the flexible tube portion 10 having the cylindrical-shaped outer cover 12 on the outer circumference thereof.

Note that, inside the mesh tube 11, a flex tube as a core member that prevents crushing of the flexible tube portion 10 is provided, though not shown. The flex tube is formed by spirally winding an elongated metallic thin plate around an axis along the longitudinal direction of the flexible tube portion 10. The width of the thin plate constituting the flex tube is narrower than a pitch width of the wound thin plate, the flex tube deforms in accordance with the curve of the flexible tube portion 10.

Inside the flexible tube portion 10 configured as described above, in addition to the above-described rigidity changing mechanism portion 20, internal components such as an electric cable that electrically connects the image pickup unit and the endoscope connector, conduits through which fluid, a treatment instrument, etc., are passed are inserted. Since the internal components other than the rigidity changing mechanism portion 20 are known techniques, descriptions thereof will be omitted.

The rigidity changing mechanism portion 20 includes a coil pipe 22, a first wire 24, and a second wire 26, which are linear members. With regard to the members constituting the rigidity changing mechanism portion 20, the direction toward the distal end portion 8 of the insertion portion 2 is referred to as a distal end direction and the direction toward the operation portion 3 is referred to as a proximal end direction.

The coil pipe 22 is a linear member formed by winding a linear element wire made of metal such as stainless alloy spirally around a predetermined axis A parallel to the longitudinal direction of the insertion portion 2.

The diameter of the element wire constituting the coil pipe 22 is larger than a maximum gap created between the thin wires adjacent to each other in the mesh tube 11. In other words, the maximum dimension of the gap created in the mesh tube 11 is smaller than the diameter of the element wire of the coil pipe 22.

The proximal end 22b of the coil pipe 22 is held by a coil fixing portion 23 fixed to the operation portion 3. The coil pipe 22 includes, inside thereof, a space having a predetermined inner diameter, with the predetermined axis A as a center. The first wire 24 to be described later is inserted in the coil pipe 22.

The first wire 24 is a linear member inserted in the coil pipe 22 and formed by intertwining linear element wires made of metal. The first wire 24 is formed by intertwining the element wires made of stainless alloy, for example.

The diameter of the first wire 24 is larger than the maximum gap created between the thin wires adjacent to each other in the mesh tube 11. In other words, the maximum dimension of the gap created in the mesh tube 11 is smaller than the diameter of the first wire 24.

The element wires of the first wire 24 have a diameter smaller than that of the element wire constituting the coil pipe 22. The rigidity of the element wires of the first wire 24 is lower than the rigidity of the outer cover 12, and the element wires of the first wire 24 have such a strength that the element wires do not pierce the surface of the outer cover 12. For example, even if the element wires of the first wire 24 are butted against the outer cover 12 from the direction perpendicular to the outer cover 12, the first wire 24 is buckle-deformed without piercing the outer cover 12.

A distal end 24a of the first wire 24 inserted in the coil pipe 22 is engaged with a distal end 22a of the coil pipe 22 such that a force compressing the coil pipe 22 along the axis A is applied to the coil pipe 22 when the first wire 24 is pulled in the proximal end direction.

Specifically, the distal end 24a of the first wire 24 protrudes in the distal end direction with respect to the distal end 22a of the coil pipe 22. A connecting portion 25 having an outer shape larger than the inner diameter of the coil pipe 22 is secured at the distal end 24a of the first wire 24. That is, the relative movement of the distal end 24a of the first wire 24 in the proximal end direction with respect to the distal end 22a of the coil pipe 22 is restricted by the connecting portion 25.

In addition, the connecting portion 25 is secured to the distal end 22a of the coil pipe 22 by adhesive, soldering, or brazing. That is, the distal end 24a of the first wire 24 is fixed to the distal end 22a of the coil pipe 22. Note that the distal end 24a of the first wire 24 may be directly secured to the distal end 22a of the coil pipe 22 by adhesive, soldering or brazing without using the connecting portion 25.

As described above, the proximal end 22b of the coil pipe 22 is fixed to the operation portion 3 with a coil fixing portion 23. Therefore, when the first wire 24 is pulled in the proximal end direction, the tensile force applied to the first wire 24 is transmitted to the distal end 22a of the coil pipe 22, and the compression force in the direction of the axis A is applied to the coil pipe 22. The compression force is applied to the coil pipe 22, to thereby increase the resistance force of the coil pipe 22 against bending deformation. The greater the compression force applied to the coil pipe 22, the greater the resistance force of the coil pipe 22 against bending deformation.

The proximal end 24b of the first wire 24 is connected to the pulling mechanism portion 30 that pulls the first wire 24 in the proximal end direction to apply a tensile force to the first wire 24.

Since the pulling mechanism portion 30 is known, detailed description thereof will be omitted. In the present embodiment, as one example, the pulling mechanism portion 30 includes a rigidity changing knob 21 that rotates with respect to the operation portion 3 and a wire holding portion 30a that holds the proximal end 24b of the first wire 24 and advances and retracts in the direction along the axis A in accordance with the rotation of the rigidity changing knob 21.

A cam groove 21b is carved on the inner circumferential surface of the rigidity changing knob 21. The wire holding portion 30a is disposed in the operation portion 3 so as to be able to advance and retract in the direction along the axis A. In addition, the wire holding portion 30a includes a cam pin 30b that is slidably engaged with the cam groove 21b. The engagement between the cam groove 21b and the cam pin 30b causes the wire holding portion 30a to advance and retract in the direction along the axis A in accordance with the rotation of the rigidity changing knob 21. The pulling mechanism portion 30 configured as described above in the present embodiment is capable of changing the tensile force to be applied to the first wire 24 in accordance with the rotation operation of the rigidity changing knob 21 by a user.

The second wire 26 is a linear member formed by intertwining the linear element wires made of metal. The second wire 26 is formed by intertwining the element wires made of stainless alloy or the like, for example.

The diameter of the second wire 26 is smaller than the diameter of the first wire 24, but larger than the maximum gap created between the thin wires adjacent to each other in the mesh tube 11. In other words, the maximum dimension of the gap created in the mesh tube 11 is smaller than the diameter of the second wire 26.

The element wires of the second wire 26 have a diameter smaller than that of the element wires of the first wire 24. In addition, the element wires of the second wire 26 are made of a material having a tensile strength smaller than that of the element wires of the first wire 24. The diameter of the second wire 26 is smaller than that of the first wire 24.

The rigidity of the element wires of the second wire 26 is lower than the rigidity of the outer cover 12, similarly as the element wires of the first wire 26, and the element wires of the second wire 26 have such a strength that the element wires do not pierce the surface of the outer cover 12. For example, even if the element wires of the second wire 26 are butted against the outer cover 12 from the direction perpendicular to the surface of outer cover 12, the second wire 26 is buckle-deformed without piercing the outer cover 12.

The second wire 26 is fixed to the constituent member of the insertion portion 2 in the state where the rotation of the distal end 26a is restricted, and the proximal end 26b is fixed to the distal end 24a of the first wire 24. That is, the second wire 26 is arranged on the distal end side with respect to the first wire 24.

Specifically, the distal end 26a of the second wire 26 is fixed to a wire fixing portion 28 of a barrel member 9a arranged at the proximal end of the bending portion 9 of the insertion portion 2 in the state where the rotation of the distal end 26a around the axis A is restricted. The distal end 26a of the second wire 26 is secured to the wire fixing portion 28 by adhesive, soldering, brazing, or the like, for example.

In addition, the proximal end 26b of the second wire 26 is secured to the connecting portion 25 by adhesive, soldering, brazing, or the like, for example. The distal end 24a of the first wire 24 and the proximal end 26b of the second wire 26 are secured respectively to the connecting portion 25 such that the central axes of the first and second wires are positioned on the axis A.

Note that the proximal end 26b of the second wire 26 may be secured directly to the distal end 24a of the first wire 24 by adhesive, soldering, brazing, or the like, for example, without using the connecting portion 25.

The distal end 26a of the second wire 26 is secured to the barrel member 9a of the bending portion 9, to thereby hold the position of the distal end 24a of the first wire 24 in the flexible tube portion 10 within the predetermined range. That is, the movable range of the distal end 22a of the coil pipe 22 in the flexible tube portion 10 is determined by the second wire 26. Therefore, the coil pipe 22 is held so as to be movable only within the range determined by the second wire 26, when the first wire 24 is pulled in the proximal end direction by the pulling mechanism portion 30, or when the flexible tube portion 10 is repeatedly curved.

As described above, the resistance force of the coil pipe 22 against the bending deformation changes according to the tensile force applied to the first wire 24 by the pulling mechanism portion 30. Therefore, the rigidity of the flexible tube portion 10 against curve in the range in which the coil pipe 22 is arranged changes according to the resistance force of the coil pipe 22 against the bending deformation. With the above-described configuration, the rigidity changing mechanism portion 20 changes the rigidity of at least a part of the insertion portion 2.

As described above, the rigidity changing mechanism portion 20 in the endoscope 1 according to the present embodiment includes the coil pipe 22, the first wire 24, and the second wire 26 that are linear members inserted in the flexible tube portion 10. In addition, the flexible tube portion 10 that encloses the circumferences of the linear members includes the mesh tube 11 formed by braiding the thin wires in a tubular shape, and the outer cover 12 that covers the outer circumference of the mesh tube 11.

In the present embodiment, the maximum dimension of the gap created between the thin wires adjacent to each other in the mesh tube 11 is smaller than the diameter of the element wire of the coil pipe 22. Therefore, even if the coil pipe 22 is broken when the flexible tube portion 10 is curved to a bending radius smaller than the predetermined allowable bending radius in the state where the coil pipe 22 is compressed by the first wire 24 being pulled by the pulling mechanism portion 30, for example, the element wire constituting the coil pipe 22 does not protrude outside of the mesh tube 11. Therefore, the present embodiment prevents the element wire of the coil pipe 22 from contacting the outer cover 12 when the coil pipe 22 is broken, to thereby be capable of preventing damage on the outer cover 12.

In addition, the maximum dimension of the gap created between the thin wires adjacent to each other in the mesh tube 11 is smaller than the diameters of the first wire 24 and the second wire 26. Therefore, even if the first wire 24 or the second wire 26 are cut, the first wire 24 or the second wire 26 does not protrude outside the mesh tube 11. The present embodiment prevents the first wire 24 or the second wirer 26 from contacting the outer cover 12 when the first wire 24 or the second wire 26 is cut, to thereby be capable of preventing the damage on the outer cover 12.

Since the diameters of the element wires constituting the first wire 24 and the second wire 26 are smaller than the maximum dimension of the gap created between the thin wires adjacent to each other in the mesh tube 11, when the cut first wire 24 or second wire 26 are loosened, there is a possibility that some of the element wires penetrate through the mesh tube 11 to contact the outer cover 12. However, in the present embodiment, the rigidities of the element wires constituting the first wire 24 and the second wire 26 are lower than the rigidity of the outer cover 12. Therefore, even if the element wires themselves contact the outer cover 12, damage on the outer cover 12 is prevented.

As described above, with the endoscope 1 according to the present embodiment, even in the case where the coil pipe 22, the first wire 24, and the second wire 26, which are included in the rigidity changing mechanism portion 20 and are linear members inserted through the insertion portion 2 are damaged, the outer cover 12 covering the outer circumference of the insertion portion 2 is prevented from being damaged, which enables the watertightness of the insertion portion 2 to be maintained.

Note that, as another embodiment, even if the rigidity of the element wires constituting the first wire 24 is made higher than the rigidity of the outer cover 12, damage on the outer cover 12 can be prevented by making the diameter of each of the element wires of the first wire 24 smaller than the maximum dimension of the gap of the coil pipe 22 and making the rigidity of the element wires constituting the second wire 26 lower than the rigidity of the outer cover 12. That is, the rigidities of the element wires of the wire and the coil that are exposed so as to face the inner surface of the flexible tube portion 10 are made lower than the rigidity of the outer cover 12, thereby enabling prevention of the damage on the outer cover, as the objective of the present invention.

In addition, the present invention is applicable not only to the linear members included in the rigidity changing mechanism portion 20 but also to linear members such as other wires inserted in the insertion portion 2. For example, as is known, bending operation wires for performing bending operation of the bending portion 9 are inserted in the insertion portion 2, for example. The bending operation wires are pulled in accordance with the rotation of the angle operation knob 6, to cause the bending portion 9 to bend. When the present invention is applied to the bending operation wires, either the diameter of each of the bending operation wires or the diameter of each of the element wires of the bending operation wires is set to be larger than the maximum dimension of the gap created between the thin wires adjacent to each other in the mesh tube 11. In addition, when the diameter of each of the element wires of the bending operation wires is smaller than the maximum dimension of the gap created between the thin wires adjacent to each other in the mesh tube 11, the rigidity of the element wires is set to be lower than the rigidity of the outer cover 12. Also in this case, similarly as in the above-described embodiment, when the bending operation wires are cut, damage on the outer cover 12 covering the outer circumference of the insertion portion 2 is prevented, to thereby be capable of maintaining the watertightness of the insertion portion 2.

The present invention is not limited to the above-described embodiments, and various changes can be made, as needed, without departing from the gist or concept of the invention that can be read from claims and throughout the description. Endoscopes with such changes are also included in the technical range of the present invention.

What is claimed is:
1. An endoscope comprising:
an insertion portion formed in an elongated shape;
a mesh tube formed by braiding thin wires in a tubular shape and provided in a shape of a cylinder inside the insertion portion; and
a rigidity changing mechanism including a coil inserted in the insertion portion and formed by winding an element wire, and a wire inserted in the coil and formed by intertwining element wires, the rigidity changing mechanism being configured to apply a compression force to the coil by pulling the wire, to adjust a bending rigidity of the insertion portion,
wherein a dimension of a gap created between the thin wires in the mesh tube is set to be smaller than a diameter of the wire and larger than a diameter of each of the element wires of the wire.

2. The endoscope according to claim 1, wherein the dimension of the gap created between the thin wires in the mesh tube is set to be smaller than a diameter of the coil and a diameter of the element wire of the coil.

3. The endoscope according to claim 2, further comprising an outer cover made of resin and configured to cover an outer circumference of the mesh tube,
wherein a rigidity of the element wire of the coil is set to be lower than a rigidity of the outer cover.

4. The endoscope according to claim 1, further comprising an outer cover made of resin and configured to cover an outer circumference of the mesh tube,
wherein a rigidity of the element wires of the wire is set to be lower than a rigidity of the outer cover.

5. The endoscope according to claim 1, wherein the wire is pulled by a pulling mechanism portion provided on a proximal end side of the insertion portion.

* * * * *